US008480233B2

(12) United States Patent
Smith

(10) Patent No.: US 8,480,233 B2
(45) Date of Patent: Jul. 9, 2013

(54) LASER ILLUMINATION SYSTEM

(75) Inventor: Ronald T. Smith, Irvine, CA (US)

(73) Assignee: Alcon Research, Ltd., Fort Worth, TX (US)

(*) Notice: Subject to any disclaimer, the term of this patent is extended or adjusted under 35 U.S.C. 154(b) by 268 days.

(21) Appl. No.: 12/872,412

(22) Filed: Aug. 31, 2010

(65) Prior Publication Data

US 2012/0050684 A1    Mar. 1, 2012

(51) Int. Cl.
*A61B 3/10* (2006.01)
*A61B 3/00* (2006.01)

(52) U.S. Cl.
USPC ............. 351/221; 351/245; 606/4; 606/15

(58) Field of Classification Search
USPC .................................. 351/221; 600/179
See application file for complete search history.

(56) References Cited

U.S. PATENT DOCUMENTS

| | | | |
|---|---|---|---|
| 6,371,954 B1* | 4/2002 | Lee ................................. | 606/13 |
| 2002/0196625 A1 | 12/2002 | Krietzman | |
| 2007/0073275 A1* | 3/2007 | Conston et al. .................. | 606/6 |
| 2007/0167681 A1* | 7/2007 | Gill et al. ...................... | 600/112 |
| 2008/0246920 A1* | 10/2008 | Buczek et al. ................ | 351/221 |
| 2010/0067658 A1 | 3/2010 | Gertner et al. | |
| 2010/0106146 A1 | 4/2010 | Boitor et al. | |
| 2010/0121198 A1 | 5/2010 | West et al. | |
| 2010/0182569 A1* | 7/2010 | Artsyukhovich et al. ...... | 351/221 |
| 2011/0037948 A1* | 2/2011 | Horvath et al. ............... | 351/221 |
| 2011/0149247 A1* | 6/2011 | Artsyukhovich ............. | 351/221 |
| 2011/0282160 A1* | 11/2011 | Bhadri et al. ................. | 600/236 |
| 2012/0130358 A1* | 5/2012 | Cisel et al. ..................... | 606/10 |

* cited by examiner

*Primary Examiner* — Jordan Schwartz
(74) *Attorney, Agent, or Firm* — Darrien Reddick

(57) ABSTRACT

An ophthalmic endoillumination system comprises a self-contained power source and a laser light source powered by the self-contained power source to produce light. The system further comprises an elongated member sized for insertion into an eye and for conducting the light produced by the laser light source.

11 Claims, 3 Drawing Sheets

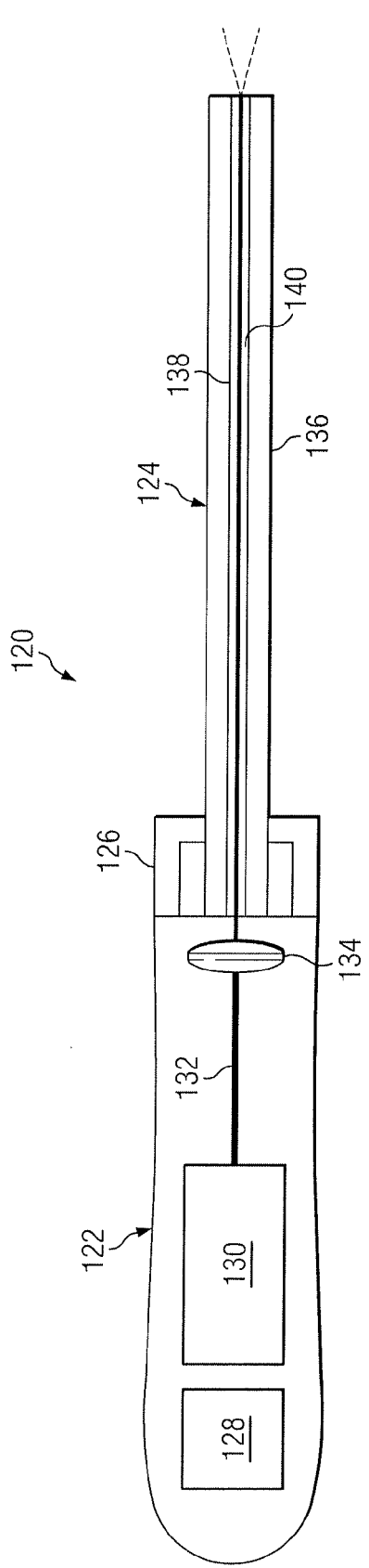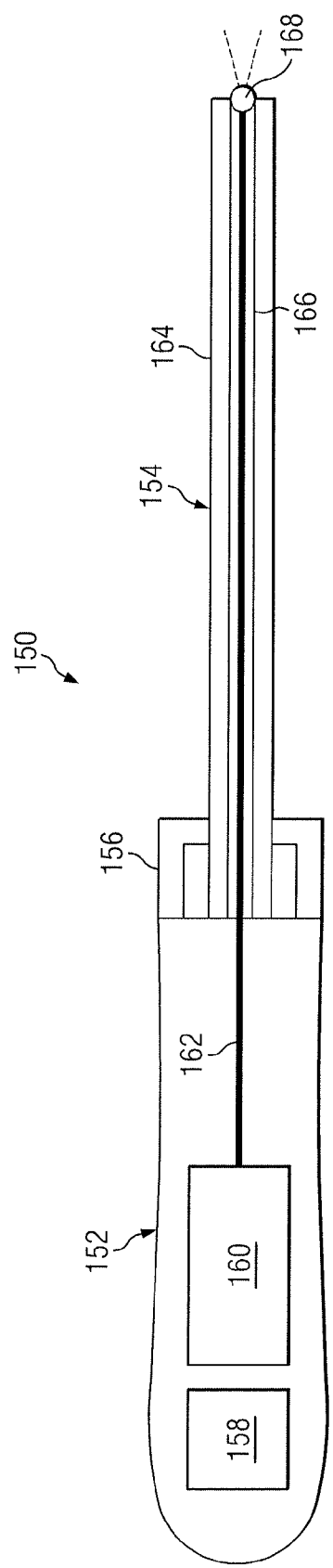

LASER ILLUMINATION SYSTEM

TECHNICAL FIELD

This disclosure relates in general to an endoillumination system and more particularly to an ophthalmic endoillumination system with a laser light source.

BACKGROUND

Anatomically, the eye is divided into two distinct parts—the anterior segment and the posterior segment. The anterior segment includes the lens and extends from the outermost layer of the cornea (the corneal endothelium) to the posterior of the lens capsule. The aqueous humour fills the space between the lens and the cornea and helps maintain intraocular pressure. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of approximately 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. In a process known as vitreous syneresis, the collagen of the vitreous body may break down and result in retinal detachment.

Vitrectomy and other vitreoretinal surgical procedures are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a minimally invasive light source to illuminate inside the eye, an infusion line to maintain the eye's shape during surgery, and instruments to cut and remove the vitreous body.

During such surgical procedures, proper illumination of the inside of the eye is important. Often, an endoilluminator containing a thin probe is inserted into the eye to provide the illumination. The probe may be optically connected to a light source, such as a metal halide lamp, a halogen lamp, or a xenon lamp, which is often used to produce the light carried by the optical probe into the eye. This endoillumination system configuration may be large, expensive, and non-portable. Alternatively, one or more light emitting diodes (LED's) may provide the light source for the optical probe. However, LED's may be unsuitable for use in some cordless, handheld devices because the power required to achieve sufficient luminance results in poor battery life and may generate enough heat to cause the handheld device to get dangerously hot.

New systems and methods are needed for illuminating the inside of the eye using a portable, high luminance light source.

SUMMARY

In one exemplary aspect, an ophthalmic endoillumination system comprises a self-contained power source and a laser light source powered by the self-contained power source to produce light. The system further comprises an elongated member sized for insertion into an eye and for conducting the light produced by the laser light source.

In another exemplary aspect, a method for endoillumination of an interior body region comprises selecting an endoillumination system. The endoillumination system includes a self-contained power source, a laser light source for producing light, and an elongated member sized for insertion into an eye and for conducting the light produced by the laser light source. The method further includes inserting at least a portion of the elongated member into the interior body region and illuminating the interior body region with the produced light from the laser light source.

In another exemplary aspect, an ophthalmic endoillumination system comprises a housing sized for carriage and manipulation by a human hand. The housing contains a battery and a laser light source for producing light. The system further comprises an elongated probe with proximal and distal ends. The proximal end is connected to the housing and the distal end is sized for insertion into an eye. The elongated probe includes a cannula sized to transmit the produced light. The system further comprises an optical component located at the distal end of the elongated probe to alter the angular dispersion of the produced light.

Further aspects, forms, embodiments, objects, features, benefits, and advantages of the present invention shall become apparent from the detailed drawings and descriptions provided herein.

BRIEF DESCRIPTION OF THE DRAWINGS

FIGS. 2 and 3 are cross sectional schematic views of handheld endoillumination systems comprising a single laser light source according to embodiments of the present disclosure.

DETAILED DESCRIPTION

Figure 1:
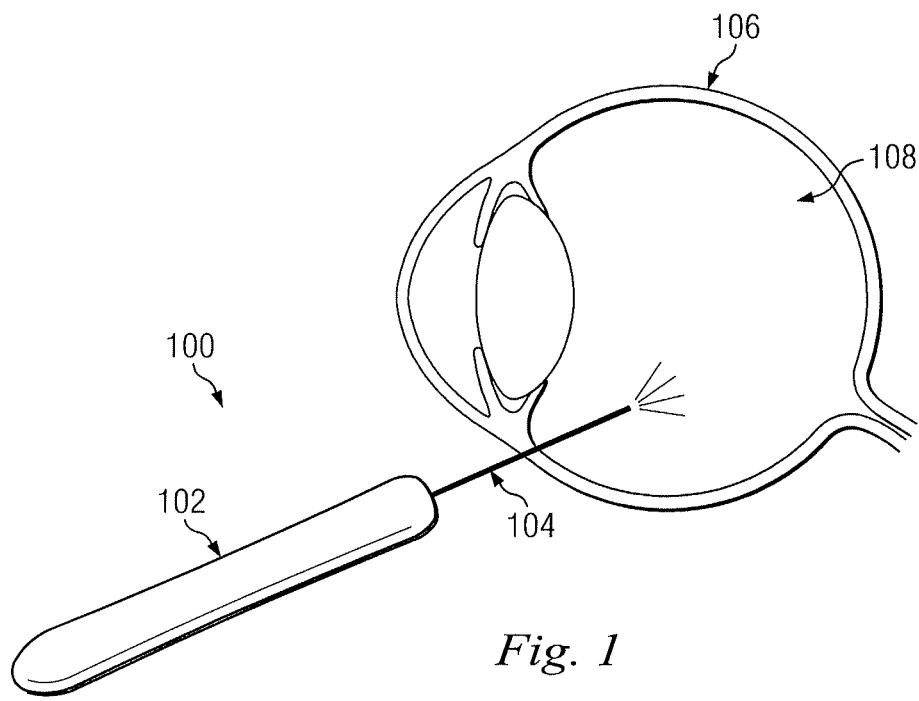
FIG. 1 is a diagram of an endoillumination system used for ophthalmic illumination.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows an endoillumination system 100 including a cordless hand piece 102 and a probe 104. As shown, probe 104 may be inserted into an eye 106 through an incision in the pars plana region. Probe 104 is used to illuminate the inside or vitreous region 108 of eye 106. In this configuration, the probe 104 may be used, for example, to provide illumination for vitreo-retinal surgery. Other insertion locations and surgical procedures, including surgical procedures in other areas of the body, that will benefit from the use of endoillumination will be clear to a person having ordinary skill in the art. Various alternative embodiments of the endoillumination system will be described.

For example, FIG. 2 shows an endoillumination system 120 which includes a handpiece 122 connected to a probe 124 by a connector 126. The handpiece 122 provides a housing for a power source 128 and a laser light source 130. Handpiece 122 may also include finger gripping surfaces or other ergonomic features (not shown) which allow the user to maintain a comfortable grasp and manipulate the probe 104 within an eye. The power source 128 is a self-contained power source such as a disposable battery, a rechargeable battery, a fuel cell, or other type of power source that is capable of operation without direct and continuous attachment to an electrical outlet, generator, or other centralized power source. The self-contained nature of the power source allows the endoillumination system 120 to be portable, cordless, and entirely hand-held.

The laser light source 130 generates a light beam 132 which is received by an optical component 134. In this embodiment, the optical component 134 is a condensing lens which may be, for example, a biconvex or plano-convex spherical lens, an aspheric lens, a ball lens, a gradient-index (GRIN) lens or any other type of device which can be used to focus a light beam for launching the beam into a small diameter optical fiber.

The laser light source 130 may be selected from several types of suitable lasers depending for example, upon the luminance, color, and power requirements needed. Suitable lasers may include gas lasers, semiconductor lasers, solid-state lasers, or other types known in the art. In this embodiment, the laser light source may be, for example, a diode-pumped solid state (DPSS) laser operating at a wavelength that produces green light. A diode-pumped solid state frequency doubled (DPSSFD) laser operating at approximately 532 nm may generate a particularly suitable monochromatic green output light. Using this configuration, approximately 11 lumens may be achieved at the retina using approximately 18 mW of light power.

The probe 124 includes a cannula 136 with an interior lumen 138 through which an optical fiber 140 extends. The cannula 136 may be formed from biocompatible materials and may be suitably thin and stiff for use within the vitreous region of the eye. In many embodiments, 19, 20, 23, 25, 27, or 29 gauge cannulas may be suitable. In certain embodiments, the fiber may be tapered or include other geometric features that modify the light beam. In alternative embodiments, the cannula may be omitted and the optical fiber may be used without this outer sheath.

The optical fiber 140 may be formed from a suitable glass or polymer material. Glass fiber may be particularly suitable due to its high transmittance. Glass is also a practical alternative to a polymer fiber when used in a portable, handheld device, because the light generating source is located in closer proximity to the distal end of the fiber. Because of the shorter distance involved, the optical fiber in a self-contained hand-held device may not require the same fiber flexibility as systems in which the light source is housed outside of the handpiece. The more efficient glass fiber may also be a suitable choice when used in the described laser/condensing lens configuration because the focused light beam emitted from the laser that is focused by the condensing lens may be efficiently coupled directly into a glass fiber without fiber modifications such as belling (i.e. lateral swelling) of the proximal end of the fiber. For example, a DPSSFD 532 nm laser typically has a relatively low $M^2$ factor of less than 1.2. This low $M^2$ factor corresponds to a high quality, focused light beam which may have a coupling efficiency of approximately 90%, including Fresnel reflection losses.

With the endoillumination system described in FIG. 2 and in other embodiments of this disclosure, the overall power transfer efficiency (approximately 85-90%) may be higher than conventional vitreoretinal illuminators (often 60-70%). Also because the optical fiber spans a shorter distance and does not require significant modification to control the profile of the beam, the cost of the optical fiber may be reduced compared to conventional vitreoretinal illuminators.

In the embodiment of FIG. 2, the connector 126 allows the probe 124 to be disconnected from the handpiece 122. This allows the handpiece 122 to be cleaned and reused while the probe 124 is discarded or separately sterilized. The connector 126 may be threaded, locking, snap-fit, or another type of connector known in the art.

In an alternative embodiment, as shown in FIG. 3, an endoillumination system 150 includes a handpiece 152 connected to a probe 154 by a connector 156. The handpiece 152 provides a housing for a power source 158, such as a battery, and a laser light source 160 which produces a light beam 162. The laser light source may be substantially similar to the laser light source 130 described above. In this embodiment, the probe 154 may include a cannula 164 with an interior lumen 166. Because the produced light beam 162 may be a tightly focused, collimated beam, the beam may pass through the cannula 164 without the use of an optical fiber. In this embodiment, a distal optical component 168 may be positioned at the distal end of the cannula 164 to control the spread of light across the patient's retina. Suitable optical components may include a condensing lens, a concave lens, a ball lens, and a graded index (GRIN) lens. It is understood that a distal optical component to control the angular dispersion of light may also be incorporated into embodiments in which an optical fiber is used.

Figure 4:
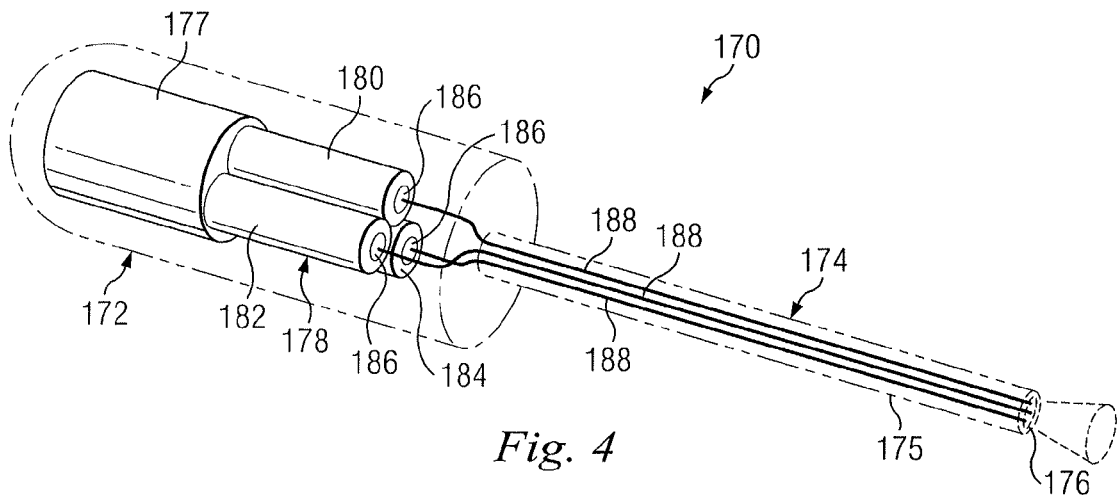
FIGS. 4-6 are perspective views of handheld endoillumination systems comprising multiple laser light sources according to embodiments of the present disclosure

In another embodiment, as shown in FIG. 4, an endoillumination system 170 includes a handpiece 172 connected to a probe 174. The probe 174 includes a cannula 175 with an interior lumen 176, which may be substantially similar to the cannula components described above. The handpiece 172 provides housing for a power source 177, such as a battery, and a laser light source 178. In this embodiment, the laser light source 178 includes three monochromatic laser light sources 180, 182, 184. The laser light sources 180, 182, 184 may be selected from several types of suitable lasers depending, for example, upon the luminance, color, and power requirements needed. Suitable lasers may include gas lasers, semiconductor lasers, solid-state lasers, or other types known in the art. In this embodiment, the laser light sources may be, for example, DPSS lasers.

The laser light source 180 operates at a wavelength between approximately 625 and 740 nm, which produces a red output light. A laser diode operating between 650 and 670 nm may generate a particularly suitable monochromatic red output light.

The laser light source 184 operates at a wavelength between approximately 520 and 565 nm, which produces a green output light. Diode pumped solid-state (DPSS) lasers that transmit at approximately 532 nm may generate a particularly suitable monochromatic green output light.

The laser light source 182 operates at a wavelength between approximately 435 and 500 nm, which produces a blue output light. Suitable blue lasers may use, for example, InGaN semiconductor lasers or DPSS lasers to generate a suitable monochromatic blue output light at a frequency between the range of 445-475 nm.

The light from each of the laser light sources 180, 182, 184 is transmitted through optical components 186, such as coupling lenses, to focus and/or direct the output light beams onto dedicated optical fibers 188 which extend through the interior lumen 176 of the cannula 175. Suitable fibers may have a diameter of less than approximately 100 although larger fibers may be appropriate for certain applications. The optical fibers 188 may terminate within, at the distal end of, or past the distal end of the cannula 175. The red, green, and blue light beams transmitted from the ends of the optical fibers 188 combine to generate a white, polychromatic, output light beam. In one example, 11 lumens of white light formed from a red beam at 632 nm, a green beam at 532 nm, and a blue beam at 473 nm would involve approximately 11 mW of red laser light, 14 mW of green laser light, and 11 mW of blue laser light, respectively. It is understood that additional optical components or optical fiber geometries (not shown) may be used to further direct and combine the monochromatic light beams into a white output beam.

Figure 5:
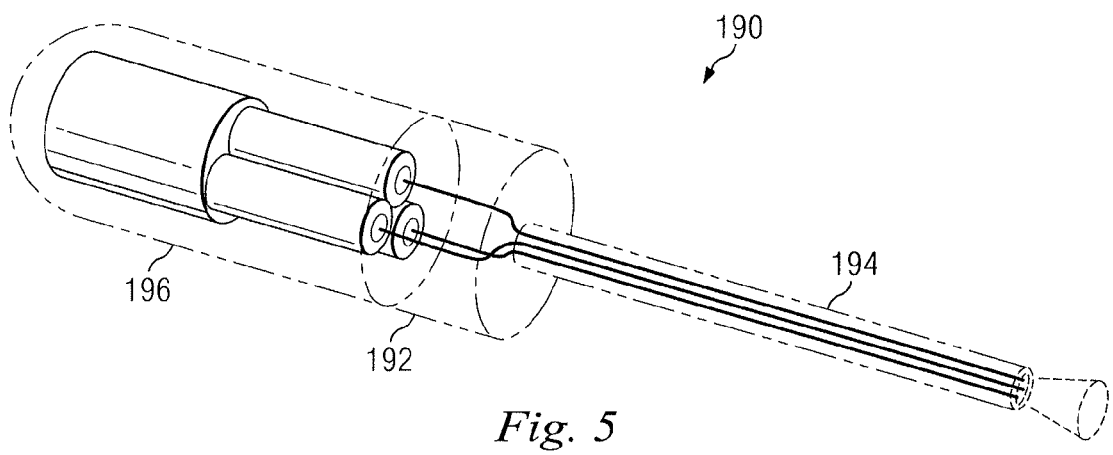

FIG. 5 depicts an endoillumination system 190 which is substantially similar to the system 170, but in this embodiment, the system further includes a connector 192 for removably connecting probe 194 to handpiece 196. As describe above for FIG. 2, the use of a connector allows the handpiece to be reused and the probe to be disposable.

Figure 6:
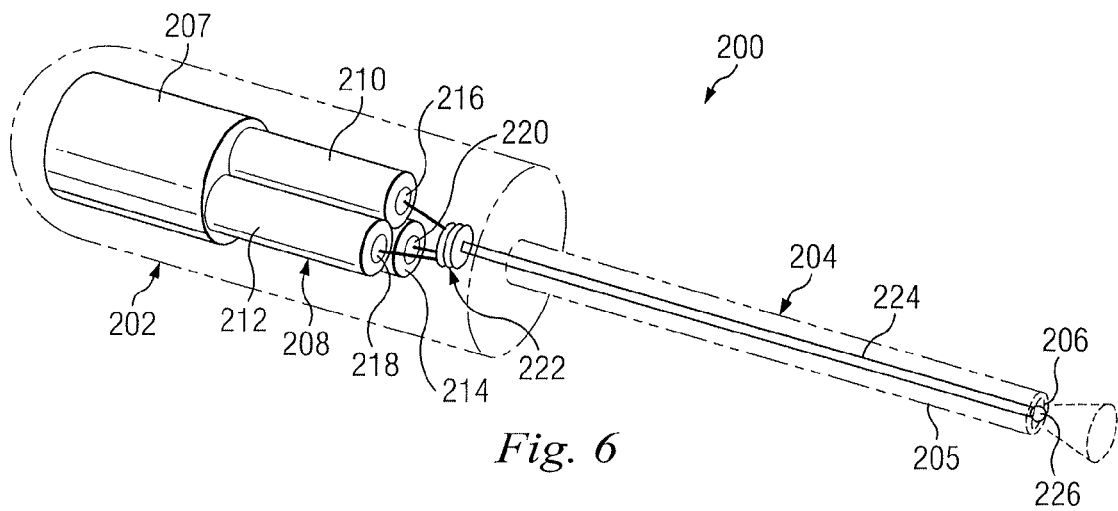

FIG. 6 depicts an endoillumination system 200 which includes a handpiece 202 connected to a probe 204. The probe 204 includes a cannula 205 with an interior lumen 206, which may be substantially similar to the cannula components described above. The handpiece 202 provides housing for a power source 207, such as a battery, and a laser light source 208. In this embodiment, the laser light source 208 includes three laser light sources 210, 212, 214 which operate to produce monochromatic red, blue, and green light, respectively. The red, blue and green light sources may be substantially similar to those described above for FIG. 4.

System 200 further includes optical components 216, 218, 220 to direct the laser light beams from the laser light sources 210, 212, 214, respectively, toward a common point. In this embodiment, the optical components 216, 218, 220 are blazed diffraction gratings tuned to the particular wavelengths of the laser light sources. The diffraction gratings can be designed for near 100% diffraction efficiency and can direct the light beams toward the common point. The endoillumination system 200 further includes a set of optical components 222 which in this embodiment are a set of stacked gratings that redirect the three light beams to create a combined coaxial beam 224 of combined red, blue, and green light. This combined "white" laser beam is collimated and narrow enough to pass through the interior lumen 206 of the cannula 205 with high efficiency and without the need for an optical fiber. In alternate embodiments, however, an optical fiber may be used. The system 200 further includes an optical component 226 located at a distal end of the cannula 205 to angularly spread the light to illuminate the retina. In this embodiment, the optical component 226 is a ball lens. In certain embodiments, the optical component that controls the angular spread of the light beam may be adjustable in response to the control of an operator or in response to sensors positioned within the illuminated region.

It is understood that the specific optical components described for use in collimating, focusing, condensing, or dispersing light are merely examples and that other types of optical components including mirrors, digital micromirror devices (DMD's), lenses, filters, reflectors, gratings, or prisms may be employed to achieve the same function. For example, the optical component for combining red, green, and blue light beams may be a dichroic prism.

Figure 7:
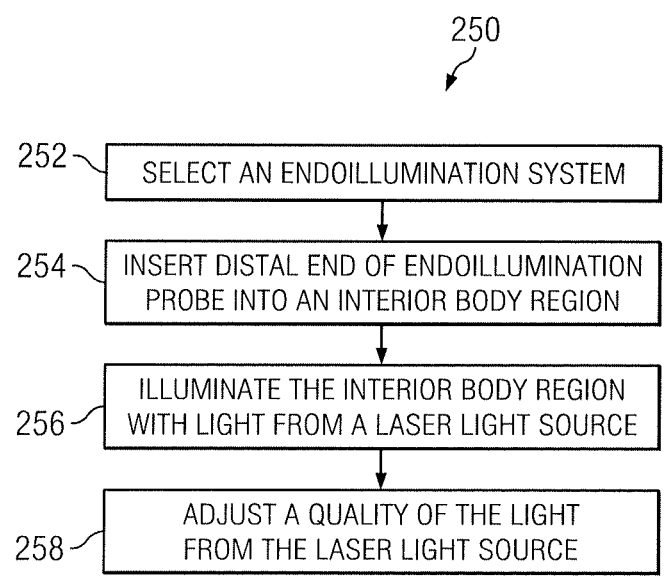
FIG. 7 is a flowchart describing a method of ophthalmic illumination.

Referring now to FIG. 7, a method 250 for interior body illumination using one of the endoillumination systems previously described is provided. At step 252, an appropriate endoillumination system is selected. Single monochromatic laser light sources such as those described in FIGS. 2 and 3 may be more energy efficient and lightweight. Some practitioners may also find that monochromatic light allows for improved visualization and differentiation of retinal tissue. Although the coherent nature of monochromatic light may cause a speckled light appearance on the retinal tissue, some practitioners may find that this actually improves retinal feature discernment. The practitioner may choose the monochromatic color most suitable for the procedure to be performed. Shorter wavelength colors, such as blue, may present a potential aphakic hazard, so endoillumination systems using laser light sources that generate these colors may further incorporate tuning mechanisms, switches, timers, or other features to minimize the exposure of tissue to the more damaging wavelengths. Longer wavelength colors, such as red, may be perceived by the human eye as less bright compared to other colors at the same power levels. Thus laser light sources that generate red light may provide less perceived luminance compared to, for example, green light at the same power.

Polychromatic laser light sources such as those described in FIGS. 4, 5, and 6 may be selected by some practitioners who prefer to work with white light. Because white light includes a larger component of shorter wavelength light (e.g., blue light) than, for example pure green light, polychromatic laser light sources may also incorporate tuning mechanisms, switches, timers, or other features to minimize the exposure of tissue to the more damaging wavelengths.

The endoillumination system may also be selected based upon the angular spread of the light at the distal end of the cannula. For example, the angular spread of light needed to illuminate the interior working area of a human eye may be smaller than for the eye of a larger animal. Likewise the interior working area of another body region of the human body may require a larger angular spread.

At step 254, the distal end of the probe is inserted into an interior body region, such as the eye. At step 256, the interior body region is illuminated with the light from the laser light source. At step 258, a quality of the light such as the angular dispersion, the color, or the brightness of the light may be adjusted. For embodiments that do not include adjustable quality parameters, this step may be omitted. After use, the endoillumination systems, such as those described in FIGS. 2, 3, and 5, that include separable probes may be disassembled. The probe portion may be discarded and the handpiece portion may be cleaned and readied for another procedure.

Although several selected embodiments have been illustrated and described in detail, it will be understood that they are exemplary, and that a variety of substitutions and alterations are possible without departing from the spirit and scope of the present invention, as defined by the following claims.

We claim:

1. An ophthalmic endoillumination system comprising:
a handpiece;
a self-contained power source housed within the handpiece;
a laser light source housed within the handpiece and powered by the self-contained power source to produce light, the laser light source comprising a plurality of lasers;
an elongated member coupled to the handpiece and sized for insertion into an eye and for conducting the light produced by the laser light source; and
at least one optical component positioned to receive and redirect a light beam from one of the plurality of lasers, wherein the at least one optical component includes a diffraction grating.

2. The ophthalmic endoillumination system of claim 1 wherein the elongated member includes a cannula.

3. The ophthalmic endoillumination system of claim 1 wherein the elongated member includes an optical fiber.

4. The ophthalmic endoillumination system of claim 1 wherein the produced light is monochromatic light.

5. The ophthalmic endoillumination system of claim 4 wherein the monochromatic light is green light.

6. The ophthalmic endoillumination system of claim 1 wherein the produced light is polychromatic light.

7. The ophthalmic endoillumination system of claim 1 wherein the plurality of lasers include a first laser for generating monochromatic blue light, a second laser for generating monochromatic red light, and a third laser for generating monochromatic green light.

8. The ophthalmic endoillumination system of claim 1 further comprising a lens arranged to receive the produced light and transmit condensed light to the elongated member.

9. The ophthalmic endoillumination system of claim 1 further comprising a lens arranged to receive the light conducted by the elongated member and to alter the angular spread of the light.

10. The ophthalmic endoillumination system of claim 1 wherein the self-contained power source includes a battery.

11. The ophthalmic endoillumination system of claim 1 further comprising a connector for removably connecting the elongated member to the handpiece.

* * * * *